(12) United States Patent
Morris et al.

(10) Patent No.: US 8,323,248 B2
(45) Date of Patent: Dec. 4, 2012

(54) MEDICAL FLUID DELIVERY SYSTEM

(75) Inventors: Mary M. Morris, Shoreview, MN (US);
Michael R. Neidert, Co. Galway (IE);
Kenneth C. Gardeski, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/822,009

(22) Filed: Jun. 23, 2010

(65) Prior Publication Data

US 2010/0262001 A1 Oct. 14, 2010

Related U.S. Application Data

(62) Division of application No. 11/097,071, filed on Mar. 31, 2005, now abandoned.

(51) Int. Cl.
*A61M 5/178* (2006.01)
(52) U.S. Cl. ............... 604/164.01; 604/508; 604/164.09
(58) Field of Classification Search .................. 604/508, 604/164.01, 164.12, 164.09, 173; 606/120, 606/126, 127
See application file for complete search history.

(56) References Cited

U.S. PATENT DOCUMENTS

| | | | |
|---|---|---|---|
| 4,106,512 A | 8/1978 | Bisping | |
| 5,354,279 A * | 10/1994 | Hofling | 604/164.12 |
| 5,983,126 A | 11/1999 | Wittkampf | |
| 6,102,887 A | 8/2000 | Altman | |
| 6,228,049 B1 * | 5/2001 | Schroeder et al. | 604/93.01 |
| 6,306,124 B1 | 10/2001 | Jones et al. | |
| 6,375,615 B1 | 4/2002 | Flaherty et al. | |
| 6,478,776 B1 | 11/2002 | Rosenman et al. | |
| 6,544,230 B1 | 4/2003 | Flaherty et al. | |
| 6,591,129 B1 | 7/2003 | Ben-Haim et al. | |
| 6,602,241 B2 * | 8/2003 | Makower et al. | 604/509 |
| 6,689,099 B2 | 2/2004 | Mirzaee | |
| 6,813,521 B2 | 11/2004 | Bischoff et al. | |
| 6,905,480 B2 | 6/2005 | McGuckin et al. | |
| 2004/0097806 A1 | 5/2004 | Hunter et al. | |
| 2004/0097965 A1 | 5/2004 | Gardeski et al. | |
| 2004/0143314 A1 * | 7/2004 | Sommer et al. | 607/120 |
| 2005/0049542 A1 | 3/2005 | Sigg et al. | |

* cited by examiner

*Primary Examiner* — Laura Bouchelle
(74) *Attorney, Agent, or Firm* — Carol F. Barry

(57) ABSTRACT

A medical fluid delivery system is provided including a steerable, guide catheter, a delivery catheter adapted for deployment at a targeted tissue site using the steerable guide catheter, the delivery catheter including a proximal port, a distal port, and a lumen extending between the proximal and distal ports; a distal fixation element coupled to the delivery catheter so as to position the distal port adjacent the targeted tissue site; and a flexible hollow needle adapted to be advanced through the delivery catheter lumen, the flexible needle including a tissue-piercing distal tip for extending from the distal port of the delivery catheter for advancement into the targeted tissue site and a proximal end for extending from the proximal port of the delivery catheter through which a medical fluid is delivered.

12 Claims, 8 Drawing Sheets

MEDICAL FLUID DELIVERY SYSTEM

RELATED APPLICATION

This application is a divisional of U.S. patent application Ser. No. 11/097,071, filed Mar. 31, 2005 entitled "MEDICAL FLUID DELIVERY SYSTEM", herein incorporated by reference in its entirety.

FIELD OF THE INVENTION

The present invention relates to medical devices for delivering a medical fluid to a targeted tissue site.

BACKGROUND OF THE INVENTION

Various genetic or cellular modification therapies for treating or repairing diseased or damaged tissue are in development. For example, the delivery of skeletal myoblasts into damaged myocardium may be an effective treatment for repairing myocardial scar tissue following an infarct. Locally effective doses of a pharmacologic, genetic, or biologic agent may be toxic when given systemically. Systemic delivery of cells may be ineffective at the damaged tissue site and may be an inefficient use of specially cultured or harvested cells. Therefore, it is desirable to provide a fluid-delivery device and method for delivering cells or another genetic or biologic agent locally at a targeted tissue site.

Drug-eluting leads are commercially available and used for delivering, for example, an anti-inflammatory agent at an implant site. Drug-eluting devices are generally limited to treating only a relatively small volume of tissue at a device-tissue interface. The pharmacological effect is in part limited by the kinetics of the drug leaving the device. Biologic and genetic agents may have a limited shelf life, requiring unique storage conditions such as refrigeration, and may not tolerate sterilization procedures. Therefore, it is not desirable to package a device having drug eluting capabilities with the biologic or genetic agent already incorporated therein. To take advantage of various genetic or cellular modification therapies, it is desirable to provide a delivery device that allows a pharmaceutical, genetic, or biologic agent to be delivered to a targeted site at a depth within the tissue to treat a volume of tissue.

BRIEF SUMMARY OF THE INVENTION

The present invention provides a medical fluid delivery system and method for targeted delivery of cells or a biologic, genetic, or pharmaceutical agent, all of which are generically referred to herein as a "medical fluid". The delivery system includes a steerable guide catheter having an open lumen for carrying a delivery catheter. The delivery catheter is provided with a fixation member for anchoring the distal end of the delivery catheter adjacent to a targeted tissue site. The fixation member is provided to allow rotational movement of the delivery catheter relative to the targeted tissue site while maintaining the distal end of the delivery catheter against or near the targeted tissue surface and restricting any lateral movement of the delivery catheter relative to the targeted tissue site. In one embodiment, the fixation member is provided as helix.

The delivery catheter further includes an open lumen extending between a proximal and distal port for carrying a flexible, retractable hollow needle having a tissue-piercing distal tip. The needle can be extended from the distal port into the targeted tissue for delivering a medical fluid. In one embodiment, the flexible retractable needle is extendable from a port located on the distal end of the delivery catheter. In another embodiment, the flexible, retractable needle is extendable from a port located on the side of the delivery catheter, near its distal end. In yet another embodiment, the fixation member is provided as a hollow member and the flexible, retractable needle is extendable from the hollow fixation member. Multiple flexible, retractable needles may be provided, which are each extendable from a separate distal port. A micro-catheter that is extendable from the needle may also be provided to allow medical fluid delivery to a tissue site located more remotely from the distal needle tip.

The flexible, retractable needle is provided with a preformed curve such that the needle may be inserted into the targeted tissue site in a direction away from the fixation member along a pathway that is substantially co-planar with the targeted tissue. Alternatively, the delivery catheter lumen carrying the flexible needle may be provided with a curve near the distal port such that the flexible needle is directed along a pathway away from the fixation member, substantially co-planar with the targeted tissue.

In a method for using the fluid delivery system, the guide catheter is advanced to a targeted tissue site. The delivery catheter is anchored at the tissue site using the fixation member such that lateral movement of the delivery catheter relative to the tissue site is restricted but rotation of the delivery catheter relative to the tissue site is possible. After anchoring the delivery catheter, the steerable, guide catheter may be removed. The flexible, retractable needle is extended a desired distance into the targeted tissue and a medical fluid is delivered. The flexible, retractable needle is retracted in either a continuous or discreet step-wise fashion allowing either continuous or discreet delivery of the medical fluid along the needle path as it is retracted.

After retracting the needle, the delivery catheter remains anchored at the tissue site but is rotated a desired degree. The flexible, retractable needle is re-extended to deliver the medical fluid along a new needle path extending into the targeted tissue at a different radial direction from the delivery catheter than the first needle path. This process of rotating the delivery catheter, extending the retractable needle along a radial path from the delivery catheter, delivering a medical fluid along the needle path in either a discreet or continuous manner, and retracting the needle back into the delivery catheter is repeated as many times as desired so as to treat a volume of tissue surrounding the delivery catheter anchoring site.

In one embodiment, the fluid delivery system further includes an electrode for use in making impedance measurements between the flexible, retractable needle and the electrode. Impedance measurements performed when the needle is in an extended position can be used to determine if the delivery catheter tip is canted relative to the targeted tissue surface.

DETAILED DESCRIPTION

Figure 1:
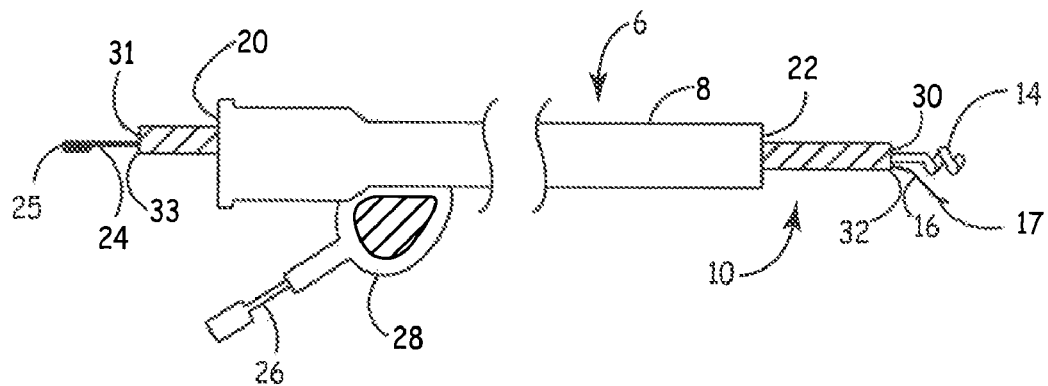
FIG. 1 is a plan view of a fluid delivery system for targeted delivery of a medical fluid.

FIG. 1 is a plan view of a fluid delivery system for targeted delivery of a medical fluid. A steerable, guide catheter 6 is provided having an elongated body 8 with an open lumen extending between a proximal end 20 and a distal end 22. A delivery catheter 10 extends through the open lumen of guide catheter 6. Delivery catheter 10 is provided with a distal fixation member 14 for anchoring the distal end 30 of delivery catheter 10 adjacent to a targeted tissue site. Delivery catheter 10 has an open lumen extending between a proximal port 33 located at or near proximal end 31 and a distal port 32 at or near distal end 30 provided for carrying a hollow, flexible needle 16 used for medical fluid delivery. Flexible needle 16 is provided with a tissue-piercing tip 17 for entering a targeted tissue site for delivery of a medical fluid. The needle 16 can be advanced and retracted with respect to delivery catheter 10 by actuating the proximal needle end 24. Needle 16 is fully retracted within the lumen of delivery catheter 10 as the guide catheter 6 is advanced to a targeted tissue site.

Guide catheter 6 is provided with a steering mechanism, which can include a manipulative handle 28 and an actuator, for example a pull wire 26, used for maneuvering the distal end 22 for steering guide catheter 6 to a targeted tissue site. Guide catheter 6 may be advanced to a targeted site using image-guidance, which may rely on fluoroscopy or other imaging technologies. Alternatively, guide catheter 6 and delivery catheter 10 may be navigated to a targeted tissue site using any appropriate navigation or localization technology such as an image-guided navigation system or other medical device mapping or localization system. Reference is made, for example, to U.S. patent application Ser. No. 10/299,969, filed Nov. 19, 2002 to Hunter et al., and U.S. Pat. No. 5,983, 126 issued to Wittkampf, both of which patents are incorporated herein by reference in their entirety. During advancement of guide catheter 6 to a targeted site, needle tip 17 is retracted within delivery catheter 10, and delivery catheter 10, including fixation member 14, is retracted within guide catheter body 6.

Upon reaching a targeted tissue site, the distal end 30 of delivery catheter 10 is anchored adjacent the targeted tissue by inserting fixation member 14 into the tissue. In an exemplary embodiment, fixation member 14 is provided as a helix such that, after anchoring delivery catheter 10 at a selected tissue site, delivery catheter 10 may be rotated relative to the tissue site but is restricted by the fixation member from moving in any lateral direction relative to the selected tissue site. The central axis of a helical fixation member 14 generally corresponds to the central axis of guide catheter 8 and delivery catheter 10. Flexible needle 16 is provided with a tissue-piercing tip 17 that is advanced a desired distance into the targeted tissue. A medical fluid can then be delivered to the targeted tissue by injecting the medical fluid through proximal opening 25 of hollow needle 16 until a desired dosage exits distal needle tip 17.

As will be described in greater detail below, delivery catheter 10 can be rotated with respect to the targeted tissue, without fully removing fixation member 14 from the tissue site, so that needle 16 may be advanced along multiple pathways extending in a generally radial direction from a single fixation site. Control of the delivery catheter rotation distance or angle may be achieved by fabricating delivery catheter 10 with a torsional stiffness that results in 1:1 matching of rotational movement between proximal end 31 and distal end 30. The distance that needle tip 17 is advanced into a targeted tissue may be controlled by providing calibrated markings near proximal needle end 24. Alternatively, rotational delivery catheter movement and needle tip advancement may be observed using medical imaging, such as fluoroscopy or measured using an a medical device mapping or localization system designed to sense rotational movement of the delivery catheter 10 about its central axis.

Figure 2:
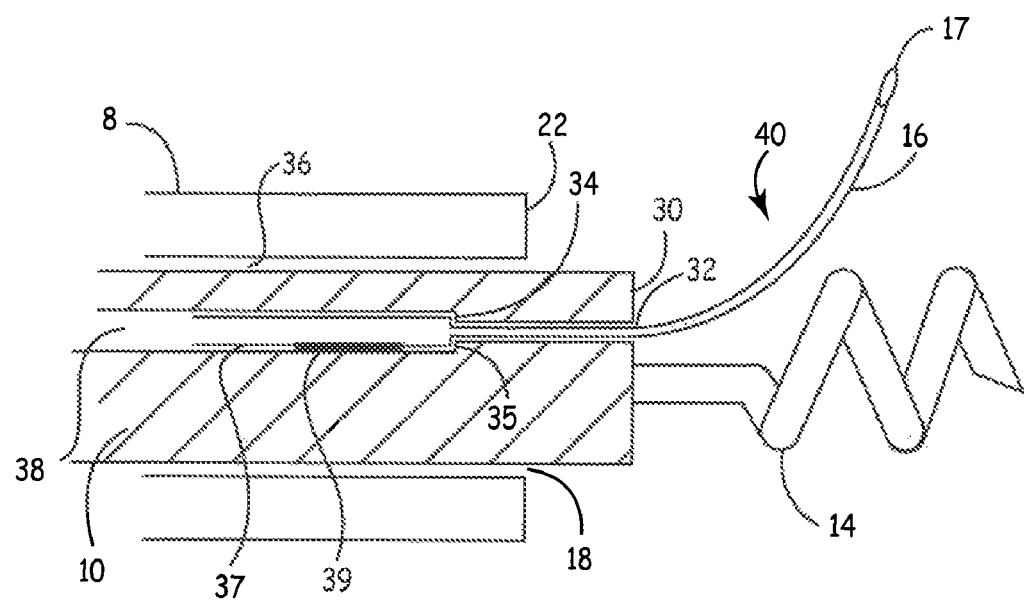
FIG. 2 is a sectional view of the distal end of the fluid delivery system shown in FIG. 1.

FIG. 2 is a sectional view of the distal end of the fluid delivery system shown in FIG. 1. Delivery catheter 10 is shown extending from the distal opening 18 of an open lumen 36 at the distal end 22 of guide catheter body 8. Delivery catheter 10 is provided with fixation member 14 and open lumen 38 for carrying flexible needle 16. Needle 16 may be provided with a laterally extending face 35 for interfacing with a lateral stop 34 provided within delivery catheter lumen 38. Lateral stop 34 limits the maximum distance that needle 16 may be extended from the distal port 32 of lumen 38 at the distal end 30 of delivery catheter 10.

In the embodiment shown in FIG. 2, needle 16 is provided as a shape-memory or super-elastic material having a pre-formed curve or bend 40 near distal tip 17. When needle 16 is retracted within lumen 38, needle 16 will be held in a straight position. When needle 16 is extended out distal port 32 and is no longer constrained by the shape of lumen 38, the native shape of needle 16 including curve 40 will be restored. Curve 40 will cause needle tip 17 to be extended in a direction away form fixation member 14, along a pathway within the targeted tissue that becomes substantially co-planar with the targeted tissue. Needle 16 can be fabricated with a pre-formed, native curve or bend using a flexible, super-elastic material or shape memory material such as Nitinol.

Flexible needle 16 and delivery catheter 10 are designed to interact in a way that allows longitudinal advancement and retraction of needle 16 but prevents rotation of needle 16 relative to delivery catheter 10 so as to maintain the direction of advancement of needle tip 17 in a radial direction away from fixation member 14. In one embodiment, flexible needle 16 is provided with a longitudinal groove 37 which interacts with a rotational stopping member 39 located along the inner diameter of delivery catheter lumen 38. Other mechanisms for preventing rotational movement of needle 16 relative to delivery catheter 10 can be substituted.

A straight needle that travels straight into the targeted tissue and remains along a pathway substantially perpendicular to the tissue plane could be used, however, a medical fluid delivered into a perpendicular needle pathway has greater likelihood of leaking out of the tissue via the needle path. Greater retention of the injected fluid within the tissue volume may be achieved when the needle pathway is substantially within a plane of the tissue substantially co-planar with the tissue rather than perpendicular to it.

Figure 3:
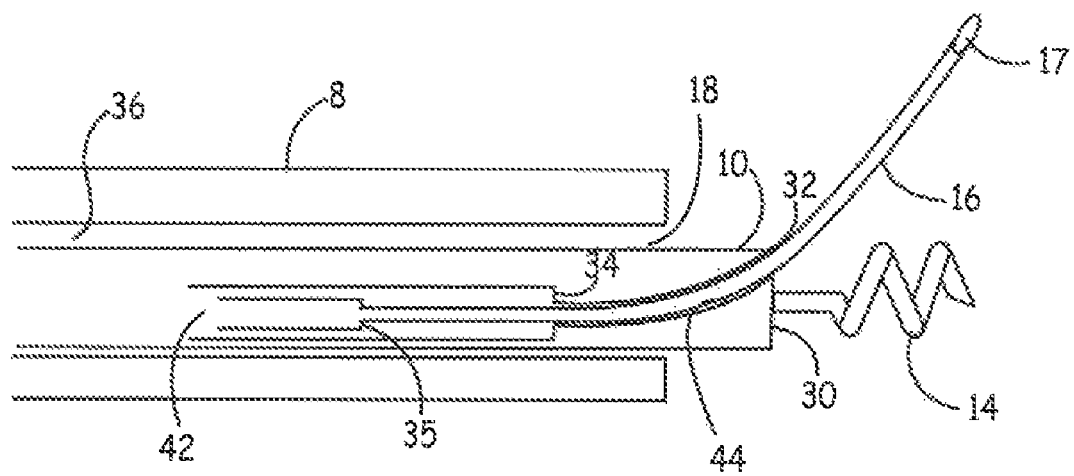
FIG. 3 is a sectional view of the distal end of a fluid delivery system according to an alternative embodiment.

FIG. 3 is a sectional view of the distal end of a fluid delivery system according to an alternative embodiment. Delivery catheter 10 extends from distal opening 18 of open lumen 36 of guide catheter 8. Delivery catheter 10 is provided with an open lumen 42 for carrying needle 16. Lumen 42 is formed with a curve 44 near distal port 32. Needle 16 is shown in a partially extended position. In a fully extended position, lateral surface 35 will interface with lateral stop 34 of lumen 42. Other retraction or advancement stop mechanisms may be incorporated in delivery catheter 10 for controlling the maximum distance that needle 16 is retracted or advanced relative to delivery catheter 10.

Needle 16 is provided as a straight or pre-formed curved, flexible, hollow needle that follows an angled pathway into targeted tissue as dictated by the geometry of curve 44. Curve 44 is designed to cause needle 16 to be directed away from fixation member 14 and enter the targeted tissue at an angle such that needle tip 17 follows a pathway that becomes substantially coplanar with the targeted tissue as needle 16 is advanced. Needle 16 may be fabricated from stainless steel or any other material that provides the lateral flexibility needed to follow the curved course of lumen 42 yet provides the longitudinal stiffness needed for insertion of needle tip 17 into a targeted tissue.

Figure 4:
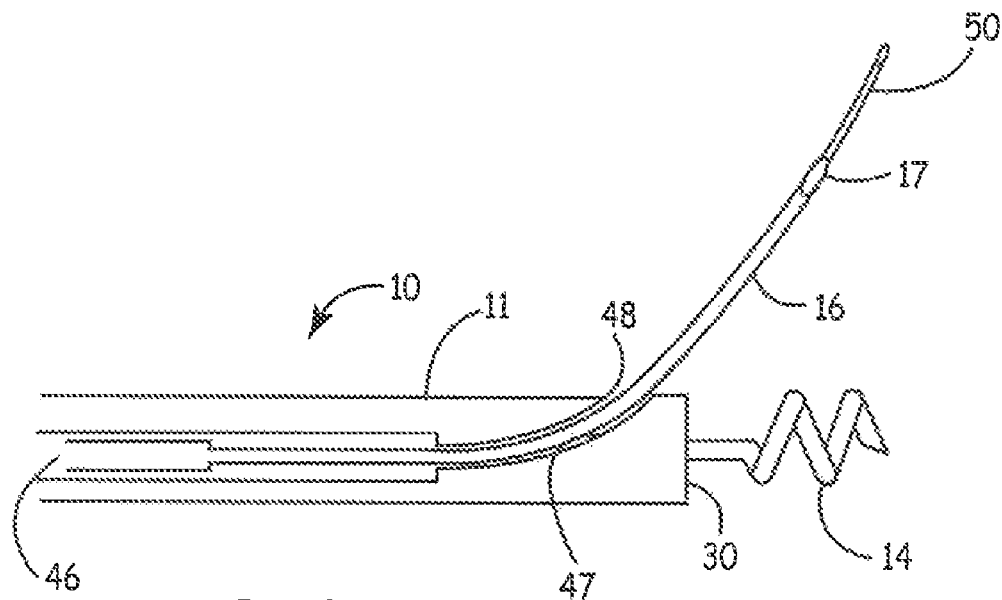
FIG. 4 is a sectional view of the distal end of a fluid delivery catheter according to another embodiment of the present invention.

FIG. 4 is a sectional view of the distal end of a fluid delivery system provided according to another embodiment of the present invention. Delivery catheter 10 is provided with a distal port 48 located on the side of delivery catheter body 11 near distal end 30. Open lumen 46 for carrying needle 16 terminates at side port 48 such that needle 16 exits delivery catheter 10 from side port 48 rather than from a port provided on distal end 30 as shown in FIGS. 2 and 3. Needle 16 may be provided as a flexible, straight needle that follows an angled pathway into a targeted tissue as dictated by curve 47 formed in lumen 46. Alternatively or additionally, needle 16 may be provided as a flexible, needle with a pre-formed distal curve near tip 17.

Figure 5:
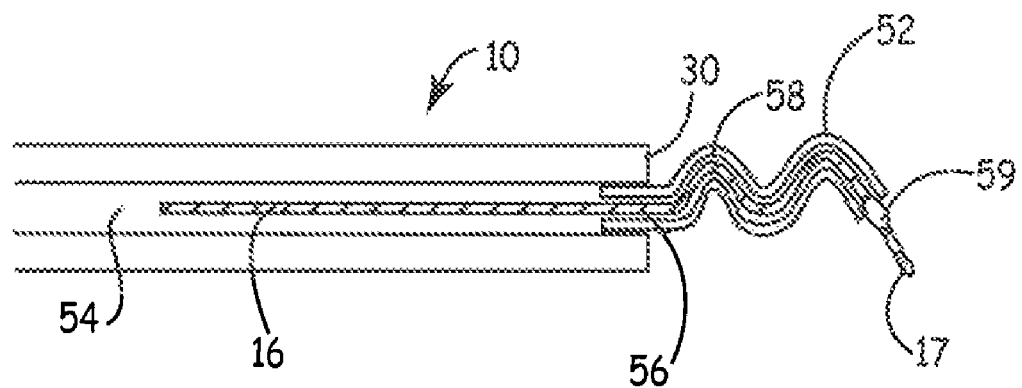
FIG. 5 is a sectional view of the distal end of a fluid delivery catheter according to yet another embodiment of the present invention.

In any of the embodiments shown in FIGS. 2, 3 and 4, a flexible microcatheter 50 may be provided extending through the length of needle 16. Microcatheter 50 can be extended through distal needle tip 17 such that a medical fluid may be delivered through microcatheter 50 into tissue located remotely from needle tip 17. The distance that the microcatheter 50 is advanced can be controlled by visualizing the microcatheter 50 using medical imaging, such as fluoroscopy. The microcatheter 50 may also be provided with calibrated markings at its distal or proximal end to allow measurement of the distance microcatheter 50 is advanced. Microcatheter 50 may be embodied as a flexible, hollow needle having a diameter smaller than needle 16 such that it may be advanced through the lumen of needle 16. In some embodiments, microcatheter 50 may be constructed as a composite of a series of tubular elements, for example as generally disclosed in U.S. Pat. No. 6,306,124, issued to Jones, et al., hereby incorporated herein by reference in its entirety. FIG. 5 is a sectional view of a fluid delivery catheter according to yet another embodiment of the present invention. Delivery catheter 10 is provided with a lumen 54 extending to a distal port 56 that is aligned with a lumen 58 included in a hollow, helical fixation member 52. Fixation member 52 is fixedly coupled to delivery catheter 10 such that delivery catheter lumen 54 and fixation member lumen 58 provide a continuous course through which flexible needle 16 may be advanced. Needle tip 17 can be extended through a distal port 59 at the distal end of the fixation member 52 into a targeted tissue after fixation member 52 is anchored at a targeted tissue site. The helical shape of fixation member 52 will direct needle tip 17 along a pathway away from fixation member 52 that is substantially co-planar with the targeted tissue. The pitch and inner diameter of hollow fixation member 52 are designed large enough to allow smooth advancement of flexible needle 16. Hollow fixation member 52 may be provided with a low-friction surface or coating on the inner surface that forms lumen 58 to promote smooth advancement of needle 16. A microcatheter extendable from needle 16 through tip 17 as described above can also be included in the delivery catheter shown in FIG. 5.

Figure 6:
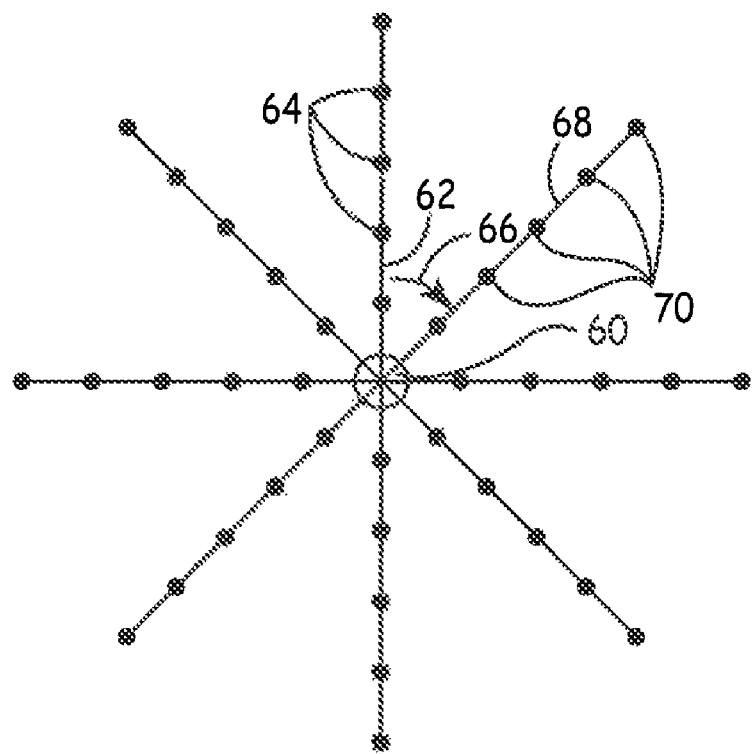
FIG. 6 is an illustration of one example of a fluid delivery pattern that can be achieved using a fluid delivery system provided by the present invention.

FIG. 6 is an illustration of one example of a fluid delivery pattern that can be achieved using a fluid delivery system provided by the present invention. Fixation site 60 is an anchoring site at a targeted tissue location in which the delivery catheter fixation member is secured. For example, site 60 may be approximately the center of a myocardial infarct that is to be treated by injecting myoblasts into the infarct area. The flexible hollow needle is extended from the delivery catheter along a needle pathway 62 a desired distance into the tissue. The view shown in FIG. 6 is looking down onto the tissue such that the plane of the paper is the plane of the myocardial tissue. The needle pathways extending from fixation site 60 are substantially co-planar with the myocardial tissue.

As the needle is retracted, the medical fluid is injected into the tissue. The medical fluid may be delivered at a controlled, continuous injection rate as the needle is retracted at a continuous or discontinuous rate. Alternatively the needle can be retracted discreet distances along needle pathway 62 with bolus injections of the medical fluid delivered at injection sites 64 at each discreet distance.

After injecting the medical fluid along pathway 62, the needle is fully retracted into the delivery catheter, and the delivery catheter is rotated. The delivery catheter is rotated a desired distance or angle 66 relative to the targeted tissue without fully removing the fixation member from the fixation site 60. The needle can then be advanced into the tissue a desired distance along a new needle pathway 68. During retraction of the needle, the medical fluid is injected continuously or at discreet injection sites 70.

These steps of advancing the needle a desired direction from the fixation site 60, injecting the medical fluid, retracting the needle back into the delivery catheter, and rotating the delivery catheter to allow needle advancement along a new pathway extending radially from fixation site 60 can be repeated as many times as desired. In the example illustrated in FIG. 6, the needle is advanced along 8 pathways (solid lines) radiating from the fixation site 60 at approximately 45 degree rotations. The medical fluid is injected at multiple sites (shown by solid circles) along each pathway. The solid circles used to indicate possible injection sites in FIG. 6 are not intended to reflect the scale of the treated tissue volume at each injection site as the distribution of the fluid will depend on the properties of both the tissue and the administered fluid.

A relatively large volume of tissue surrounding the fixation site 60 can thus be treated with a medical fluid without removing and relocating the delivery catheter. The fluid delivery system and method described in conjunction with FIG. 6 allows controlled delivery of a medical fluid within a targeted volume of tissue. The distances between delivery sites can be controlled by the controlled advancement and retracting of the needle and the rotation of the delivery catheter.

FIG. 6 is one example of a continuum of possible medical fluid delivery patterns wherein a medical fluid is delivered continuously or at one or more discreet sites located along one or more pathways extending outward from a fixation site. In order to deliver the medical fluid at sites further than the maximum distance that the needle may be advanced, a microcatheter may be advanced through the needle (as illustrated in FIG. 4), to reach tissue located remotely from the fully advanced needle tip.

Figure 7:
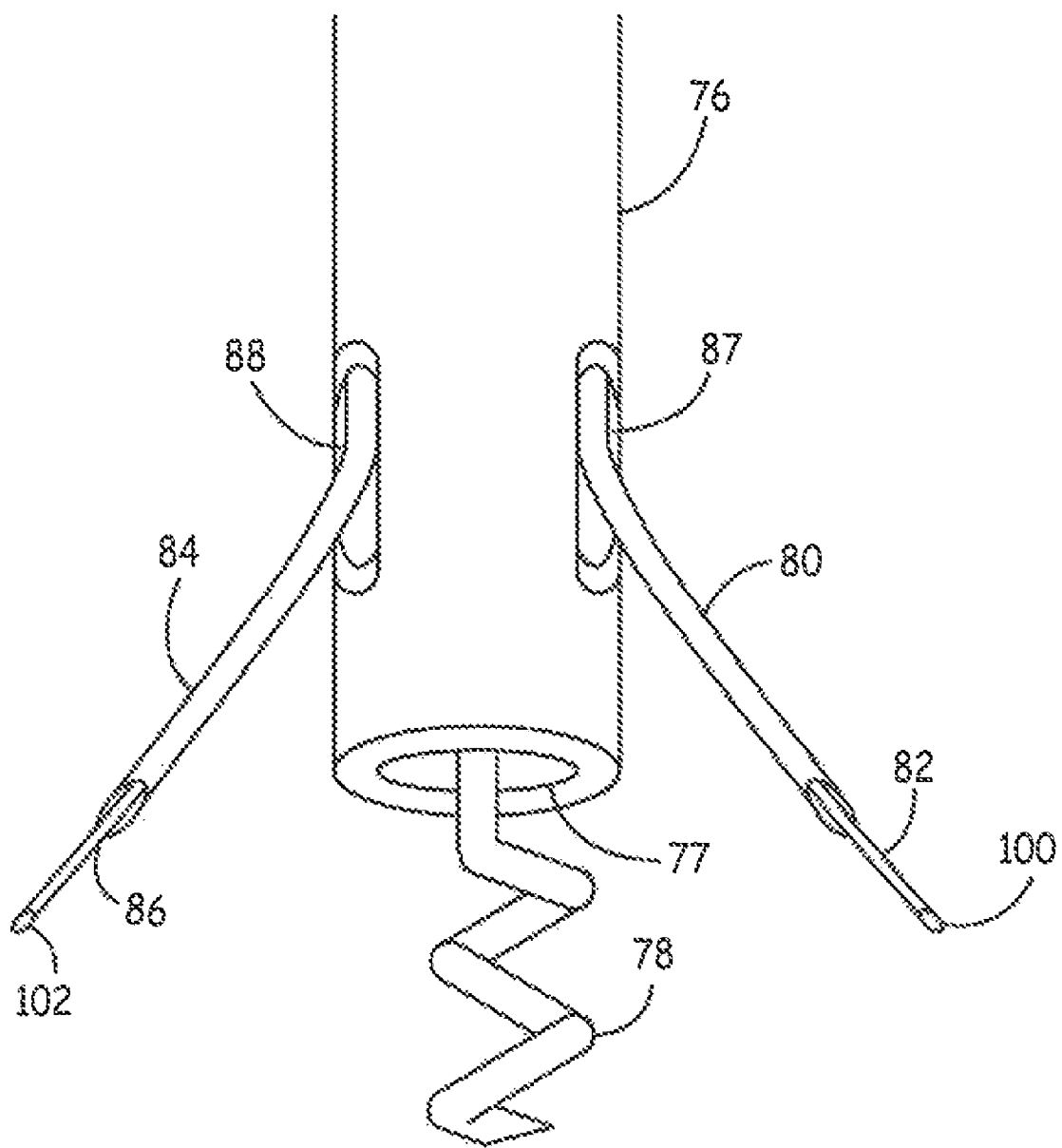
FIG. 7 is a perspective view of a delivery catheter having multiple retractable needles.

FIG. 7 is a perspective view of a delivery catheter having multiple lumens for carrying one or more flexible, retractable needles. In some embodiments, the delivery catheter may be provided with multiple needles carried individually in multiple lumens, or a single open lumen large enough to accommodate multiple needles. The multiple needles extend from separate distal ports such that they may be advanced into a targeted tissue in different radial directions away from the distal fixation member.

In the example shown in FIG. 7, two needles 80 and 84 extend from two separate distal side ports 87 and 88 of delivery catheter 76. Fixation member 78 can be provided as a retractable helix which is extended when delivery catheter 76 is positioned against a targeted tissue site. Fixation member 78 is extended from an opening 77 at the distal end of catheter 76 and anchored in the targeted tissue. Methods for implementing a retractable fixation helix are known in the art. A retractable fixation helix may be provided as generally disclosed in U.S. Pat. No. 4,106,512 issued to Bisping or as generally described in U.S. Pat. No. 6,813,521 issued to Bischoff et al., both of which patents are incorporated herein by reference in their entirety.

After securing fixation member 78 at a targeted site, needles 80 and 84 can be extended from distal side ports 87 and 88 and advanced into the targeted tissue. Microcatheters 100 and 102 are shown extending from the distal tips 82 and 86 of respective needles 80 and 84. Microcatheters may be used to deliver the medical fluid into tissue located remotely from needle tips 82 and 86. The medical fluid can be delivered along two pathways corresponding to advancing needle 80 and needle 84 simultaneously or sequentially, prior to rotating delivery catheter 76. Delivery catheter 76 may then be rotated with respect to the targeted tissue site such that needles 80 and 84 can be inserted into the targeted tissue along two new pathways.

Figure 8:
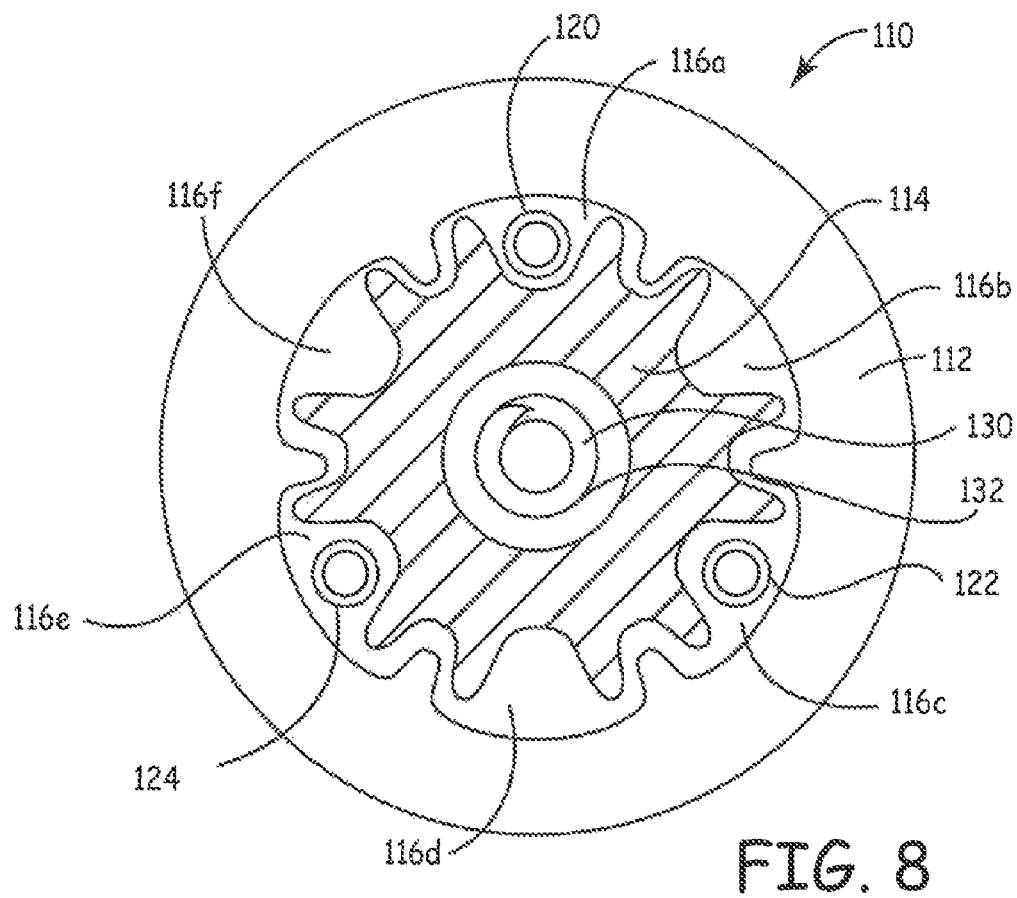
FIG. 8 is a sectional view of one embodiment of a multi-lumen delivery catheter provided with multiple needles for injecting a medical fluid into a targeted tissue.

FIG. 8 is a sectional view of one embodiment of a multi-lumen delivery catheter provided with multiple needles for injecting a medical fluid into a targeted tissue. A multi-lumen delivery catheter 110 may be provided with a splined, multi-lumen body as generally disclosed in U.S. Pat. Appl. Pub. No. 2004/0097965, by Gardeski et al., hereby incorporated herein by reference in its entirety. The elongated delivery catheter body includes an outer body member 112 having inward-radiating splines that mate with outward-radiating splines provided on an inner body member 114 so as to form multiple lumens 116a through 116f between sets of mated splines. Flexible needles 120, 122, and 124 are shown in lumens 116a, 116c, and 116e. Any or all of lumens 116a through 116f may be used for carrying flexible, hollow needles that may be advanced and retracted within lumens 116a through 116f so as to extend the needles out the distal end of the delivery catheter body to insert them into a targeted tissue site for medical fluid delivery and then retract the needles back into the catheter body during rotation or removal of the delivery catheter 110. Any remaining lumens of delivery catheter 110 not used for carrying a fluid delivery needle could be used for carrying conductors associated with distal sensors or electrodes or for carrying any other suitable medical devices or components.

Fixation member 132 may be coupled to the distal end of the inner member 114 or may be provided as a retractable fixation member housed within a central lumen 130 of inner member 114. The central lumen 130 could be counterbored at the distal end of the catheter 110 to allow a robust fixation helix 132 to be retracted into inner member 114.

Figure 9:
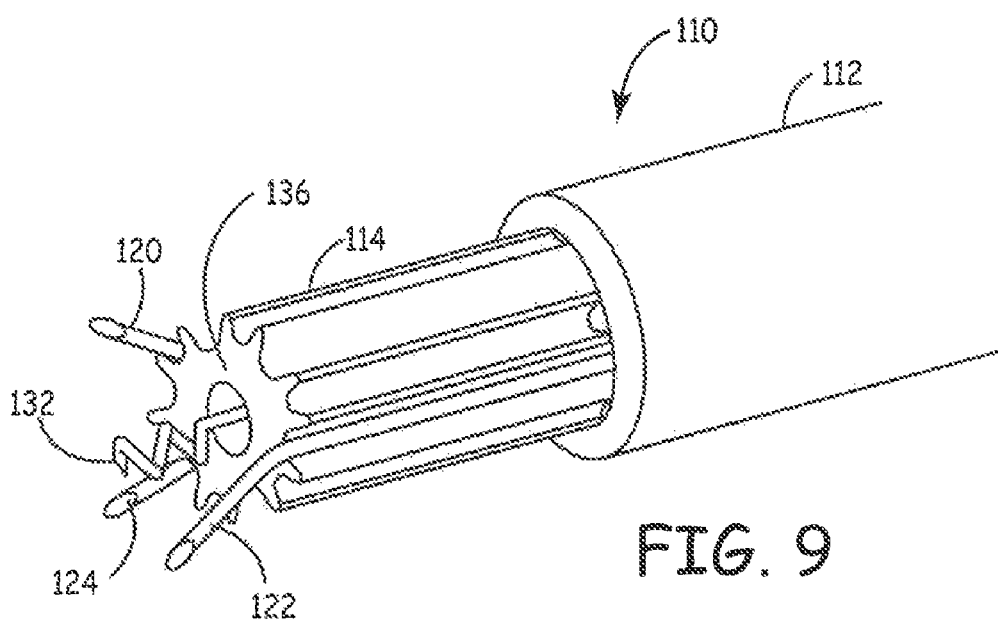
FIG. 9 is an open, perspective view of the multi-lumen delivery catheter shown in FIG. 8.

FIG. 9 is an open, perspective view of the multi-lumen delivery catheter shown in FIG. 8. Outer splined body member 112 is mated with inner splined body member 114 to form multiple lumens. Flexible needles 120, 122 and 124 may be advanced through respective lumens to extend from respective distal ports at distal end 136 of the delivery catheter 110. In an alternative embodiment, outer member 112 may be provided with side ports near distal end 136 to allow flexible needles 120, 122, and 124 to exit the catheter body via the side ports. Flexible needles 120, 122, and 124 are provided with a pre-formed curve near the distal needle tips such that the distal tips of needles 120, 122, and 124 are directed away from fixation member 132, along a pathway that becomes substantially co-planar with the targeted tissue as the needles 120, 122, and 124 are advanced.

Figure 10:
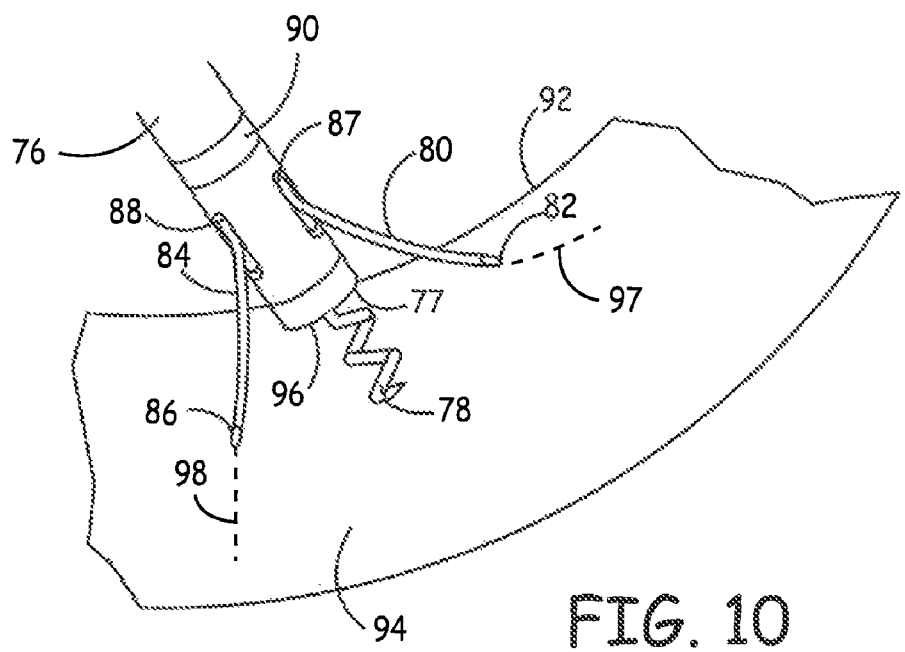
FIG. 10 shows a delivery catheter fixed at a targeted tissue site and illustrates one method for verifying the position of the delivery catheter with respect to the tissue surface.

FIG. 10 shows a delivery catheter fixed at a targeted tissue site and illustrates one method for verifying the position of the delivery catheter with respect to the tissue surface. Distal end 77 of delivery catheter 76 is positioned against the surface 92 of a targeted tissue 94. Fixation member 78 is anchored into tissue 94. Delivery catheter 76 is provided with two side ports 87 and 88 through which two flexible needles 80 and 84 are extended into a targeted tissue 94.

It is desirable to advance flexible needles 80 and 84 along pathways that are substantially co-planar with tissue 94 rather than substantially perpendicular to tissue surface 92. In order to advance needle tips 82 and 86 along a pathway that is co-planar with the targeted tissue 94, distal catheter end 77 should be positioned perpendicular against tissue surface 92 and not in a canted position as illustrated in FIG. 10. In the canted position shown, advancement of needle 84 into tissue 94 results in a needle pathway 98 substantially perpendicular to tissue surface 92. Needle 80, which enters tissue surface 92 at an angle, will follow a pathway 97 that is substantially planar with the tissue 94 but is at a shallow depth within the tissue 94.

In order to determine if the distal end 77 of delivery catheter 76 is canted relative to tissue surface 92 an impedance measurement can be made. As such, delivery catheter 76 is provided with one or more electrodes 90 and 96. Electrodes 90 and 96 are coupled to separate, insulated conductors extending to the proximal end of delivery catheter 76. In an alternative embodiment, fixation member 78 may function as an electrode for impedance measurements, in which case fixation member 78 would be coupled to a conductor extending to the proximal end of delivery catheter 76.

In one embodiment, delivery catheter 76 is used for delivering a medical fluid to myocardial tissue from an endocardial surface. As such, needles 80 and 84 will extend from side ports 87 and 88, through the intracardiac blood volume, and into the myocardial tissue 94. An impedance measurement made between needle 84 and electrode 90 will be relatively higher than an impedance measurement made between needle 80 and electrode 90 due to relatively less surface area exposure of needle 84 to the intra-cardiac blood volume.

In one method for using impedance measurements to verify the position of delivery catheter 76 relative to the tissue surface 92, two impedance measurements are made using two flexible needles 80 and 84 extended from delivery catheter 76 and a common electrode, 90 or 96. If the two impedance measurements are approximately equal, the distal end 77 of delivery catheter 76 is not canted relative to tissue surface 92. If the two impedance measurements are not substantially equal, the delivery catheter distal end 77 is canted with respect to tissue surface 92. The difference in impedance measurements arises from differing surface areas of needles 80 and 84 exposed to the intra-cardiac blood volume. Needles 80 and 84 may be retracted, and adjustment of the delivery catheter position may be made.

In another embodiment, impedance measurements may be made using one needle. The needle may be advanced into the targeted tissue and an impedance measurement made between the needle and an electrode. This impedance measurement may be compared to an expected impedance range. If the impedance measurement is outside an expected impedance range, the distal end 77 is canted with respect to tissue surface 92. A higher or lower than expected impedance measurement results when the needle surface area exposure to the intracardiac blood volume is greater or less than the surface area exposure that occurs when distal end 77 is not canted with respect to tissue surface 92.

In yet another embodiment, an impedance measurement made between one flexible needle and an electrode when the needle is extended in one direction from catheter 76 is compared to a second impedance measurement made between the same flexible needle and electrode when the needle is extending in a different direction from delivery catheter 76 after rotating catheter 76. If the two measurements are substantially equal, the surface area of the needle exposed to the blood volume is approximately equal in both positions indicating that distal end 77 is not canted relative to tissue surface 92. If the two measurements are substantially unequal, the distal end 77 of delivery catheter 76 is canted with respect to tissue surface 92. The needle can be retracted to allow adjustment of catheter 76 position.

Figure 11:
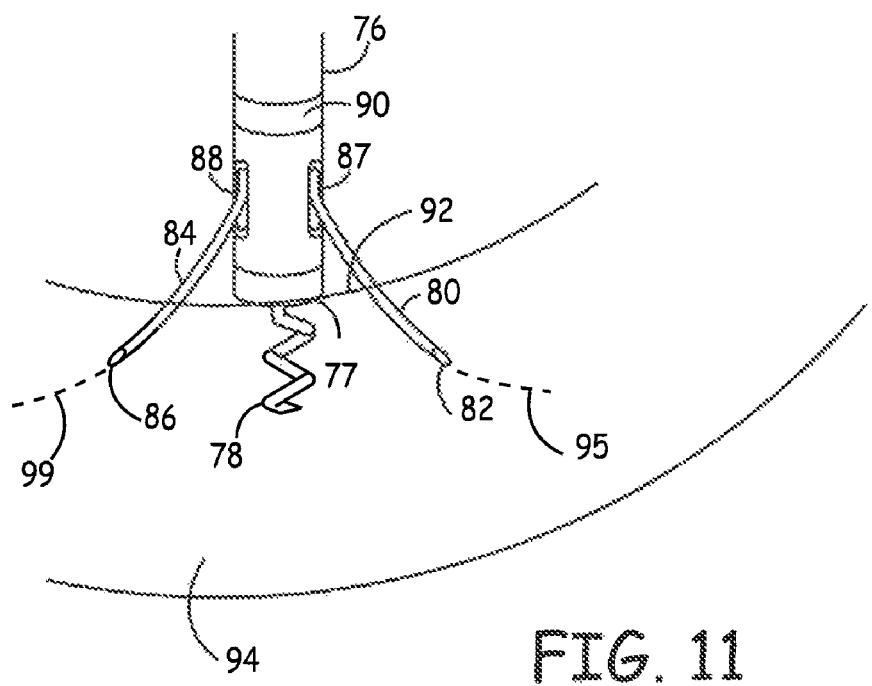
FIG. 11 shows a delivery catheter positioned perpendicularly against a targeted tissue surface.

FIG. 11 shows a delivery catheter 76 positioned perpendicularly against a targeted tissue surface. Flexible needles 80 and 84 enter tissue surface 92 at similar angles. The flexible needles 80 and 84 are fabricated with a pre-formed curve and/or are advanced through a curved lumen designed to direct the needles 80 and 84 along a pathway 95 and 99, respectively, that is approximately co-planar with the tissue 94. Impedance measurements made between needle 84 and electrode 90 and needle 80 and electrode 90 will be similar since similar surface areas of needles 80 and 84 are exposed to the intra-cardiac blood volume when the needle tips 82 and 86 are extended into the endocardial surface 92 of myocardial tissue 94.

Figure 12:
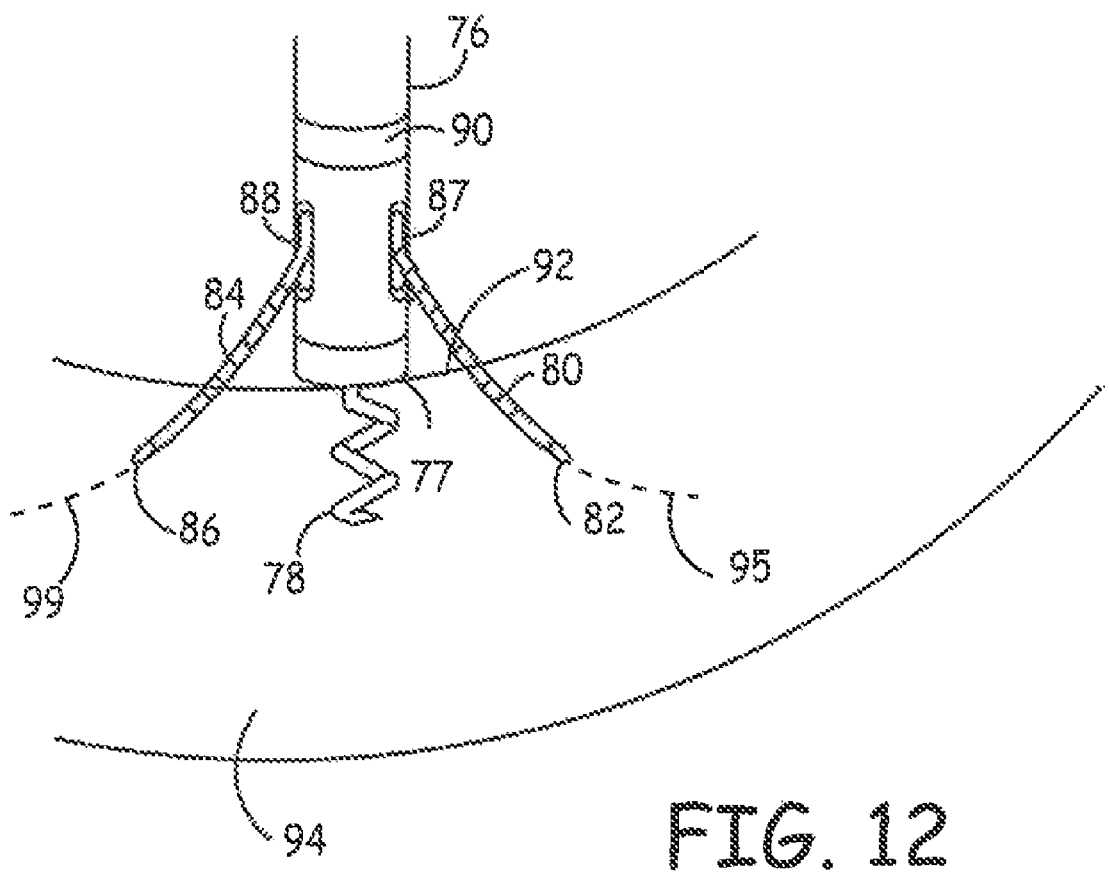
FIG. 12 shows a delivery catheter having one or more insulated needles and illustrates a method for verifying the position of a needle within a targeted tissue.

FIG. 12 shows a delivery catheter fixed at a targeted tissue site and illustrates a method for verifying the position of the hollow flexible needles 80 and 84 within the targeted tissue. Needles 80 and 84 are formed from a conductive material and are provided with insulative coating 83 and 85, respectively. For example, needles 80 and 84 may be formed from stainless steel provided with a non-conductive polymer coating, such as polyimide, a heat-shrinkable polyester, or paralyne. The insulative coating 83 and 85 insulates at least the portion of the respective needles 80 and 84 that is expected to be exposed to non-targeted tissue or body fluid when the needles 80 and 84 are advanced from delivery catheter 76. A distal portion of needles 80 and 84 near and including needle tips 82 and 86 is not insulated. An impedance measurement may then be made between needle tips 82 and 86 to verify that the needles 80 and 84 are properly inserted into the targeted tissue. Alternatively, an impedance measurement may be made between one needle tip 82 or 86 and fixation member 78, or electrode 90 for verifying that the needle tip 82 or 86 is properly inserted into the targeted tissue. The use of an impedance measurement between a needle tip and the fixation member or an electrode can be employed with fluid delivery systems having a single flexible needle.

Figure 13:
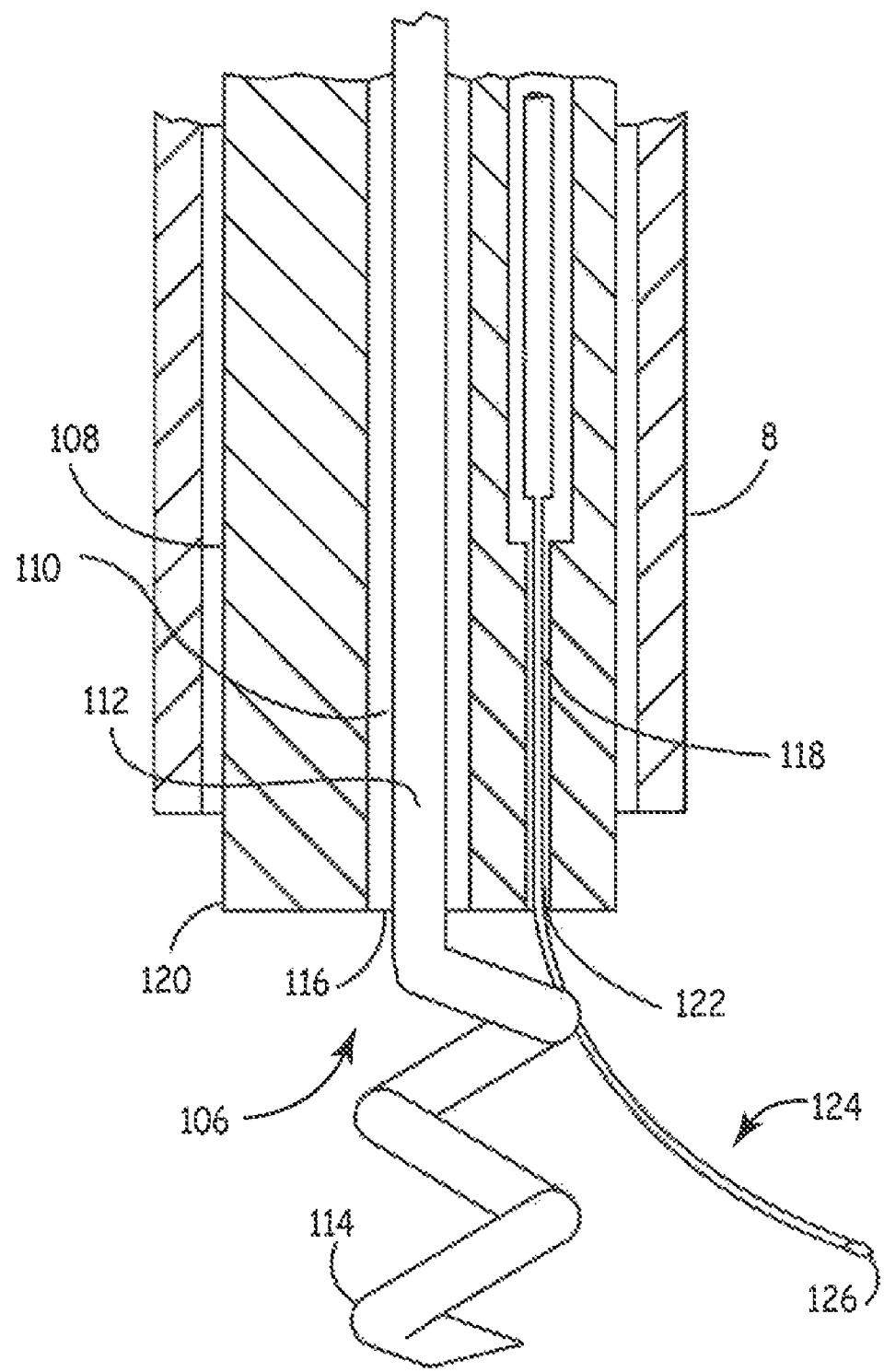
FIG. 13 is a sectional view of the distal portion of an alternative embodiment of a fluid delivery system in accordance with the invention.

FIG. 13 is a sectional view of the distal portion of an alternative embodiment of a fluid delivery system in accordance with the invention. The system includes steerable guide catheter 8 used for guiding delivery catheter 108 to a targeted tissue site. Delivery catheter 108 is provided with a central lumen 110 extending from the proximal delivery catheter end to distal end 120. Central lumen 110 is provided for carrying the elongated body 112 of fixation member 106. Fixation member 106 is provided with a tissue piercing distal end 114 which is typically formed into a helix to allow fixation member 106 to be rotated and thereby fixed into a targeted tissue site at distal end 114. The helical distal end 114 extends from central lumen opening 116 of delivery catheter 108 and is generally greater in diameter than lumen 110 such that the distal end 114 remains extended from lumen opening 116. Distal end 114 is fixed into a targeted tissue site by rotating the proximal end of elongated body 112. The proximal end of elongated body 112 may be provided with a handle (not shown) to facilitate rotation of fixation member 106.

Delivery catheter 108 is further provided with a needle lumen 118 extending from the delivery catheter proximal end to the delivery catheter distal end 120. Flexible hollow needle 124 extends through needle lumen 118 such that tissue piercing distal tip 126 can be advanced out distal opening 122 of needle lumen 118 into a targeted tissue. Distal opening 122 is shown on the distal end 120 of delivery catheter 108. Distal opening 122 may alternatively be provided on the side of delivery catheter 108, near but proximally to distal end 120. Needle 124 is provided with a preformed curve in the vicinity of distal tip 126 such that as tip 126 is advanced into a targeted tissue, it is directed away from fixation member distal end 114 and follows a needle path substantially within a plane of the targeted tissue.

After administering a fluid along a needle pathway, needle 124 can be retracted within lumen 118, delivery catheter 108 rotated with respect to fixation member 106 while fixation member 106 remains fixed in the targeted tissue, and needle 124 extended into the targeted tissue along a new pathway extending radially away from fixation member distal end 114. As such, delivery catheter 108 and fixation member 106 can be rotated independently from each other. By maintaining delivery catheter distal end 120 against the surface of the targeted tissue, a medical fluid can be delivered along multiple needle pathways at a similar depth within the tissue when fixation member 106 remains fixed in the targeted tissue.

Thus, a fluid delivery device has been described according to detailed, exemplary embodiments provided herein. The detailed descriptions are intended to illustrate various embodiments for practicing the invention and are not to be interpreted as limiting with regard to the following claims.

What is claimed is:

1. A method of delivering medical fluid to a tissue, the method comprising:
   navigating a delivery catheter body through vasculature to a fixation site of a targeted tissue;
   fixing the delivery catheter body to the fixation site using a fixation member extending from a distal end of the delivery catheter body;
   advancing a flexible needle out from a distal port located on the delivery catheter body, the flexible needle extending away from the delivery catheter body central axis and along a first pathway within the targeted tissue;

measuring a first impedance between the flexible needle and an electrode of the delivery catheter after advancing the flexible needle out from the distal port;

advancing a second flexible needle out from a second distal port located on the delivery catheter body;

measuring a second impedance using the second flexible needle after advancing the second flexible needle out from the second distal port;

verifying a position of the delivery catheter with respect to the fixation site by comparing the first impedance and the second impedance;

detecting a canted distal end of the delivery catheter body with respect to a surface of the tissue fixation site in response to the measured impedance;

adjusting the delivery catheter body position in response to detecting the canted distal end; and, delivering medical fluid through the needle to the targeted tissue along the first and second pathways.

2. The method of claim 1, wherein delivering the medical fluid comprises a continuous injection delivered along the first pathway as the needle is retracted.

3. The method of claim 1, wherein delivering the fluid comprises a plurality of bolus injections delivered at discrete locations along the first pathway as the needle is retracted.

4. The method of claim 1, wherein the flexible needle includes a pre-formed curve in proximity to the tissue-piercing distal tip such that the tip extends co-planar within the body tissue.

5. The method of claim 1, wherein the central axis of the delivery catheter body extends through the fixation member.

6. The method of claim 1, further comprising retracting the flexible needle from the first pathway of the targeted tissue, rotating the delivery catheter, while maintaining fixation at the fixation site, to reposition the distal port along a perimeter of the tissue fixation site, and, advancing the flexible needle out from the repositioned distal port into the targeted tissue.

7. A method of delivering medical fluid to a tissue, the method comprising:

navigating a delivery catheter body through a vasculature to a fixation site proximate a targeted tissue;

fixing the delivery catheter body to the fixation site using a fixation member extending from a distal end of the delivery catheter body and having a central axis that extends through the central axis of the delivery catheter body;

advancing a flexible needle out from a distal port located on the delivery catheter body, the flexible needle extending away from the delivery catheter body central axis and along a first pathway within the targeted tissue;

verifying a position of the delivery catheter with respect to the target tissue by measuring a first impedance value of the targeted tissue between the advanced flexible needle and an electrode on the delivery catheter; and delivering medical fluid through the flexible needle to the targeted tissue along the first pathway after verifying the position of the delivery catheter, wherein verifying the position of the delivery catheter with respect to the targeted tissue comprises determining that the delivery catheter is canted with respect to the surface of the tissue.

8. A method of delivering medical fluid to a tissue, the method comprising:

navigating a delivery catheter body through a vasculature to a fixation site proximate a targeted tissue;

fixing the delivery catheter body to the fixation site using a fixation member extending from a distal end of the delivery catheter body and having a central axis that extends through the central axis of the delivery catheter body;

advancing a flexible needle out from a distal port located on the delivery catheter body, the flexible needle extending away from the delivery catheter body central axis and along a first pathway within the targeted tissue;

verifying a position of the delivery catheter with respect to the target tissue by measuring a first impedance value of the targeted tissue between the advanced flexible needle and an electrode on the delivery catheter; and delivering medical fluid through the flexible needle to the targeted tissue along the first pathway after verifying the position of the delivery catheter, wherein verifying a position of the delivery catheter with respect to the targeted tissue further comprises determining that the delivery catheter is canted with respect to the surface of the targeted tissue by comparing the first impedance value to an expected impedance value for the targeted tissue.

9. A method of delivering medical fluid to a tissue, the method comprising:

navigating a delivery catheter body through a vasculature to a fixation site proximate a targeted tissue;

fixing the delivery catheter body to the fixation site using a fixation member extending from a distal end of the delivery catheter body and having a central axis that extends through the central axis of the delivery catheter body;

advancing a flexible needle out from a distal port located on the delivery catheter body, the flexible needle extending away from the delivery catheter body central axis and along a first pathway within the targeted tissue;

verifying a position of the delivery catheter with respect to the target tissue by measuring a first impedance value of the targeted tissue between the advanced flexible needle and an electrode on the delivery catheter; and delivering medical fluid through the flexible needle to the targeted tissue along the first pathway after verifying the position of the delivery catheter, wherein the electrode on the delivery catheter comprises the fixation member.

10. A method of delivering medical fluid to a tissue, the method comprising:

navigating a delivery catheter body through a vasculature to a fixation site proximate a targeted tissue;

fixing the delivery catheter body to the fixation site using a fixation member extending from a distal end of the delivery catheter body and having a central axis that extends through the central axis of the delivery catheter body;

advancing a flexible needle out from a distal port located on the delivery catheter body, the flexible needle extending away from the delivery catheter body central axis and along a first pathway within the targeted tissue;

verifying a position of the delivery catheter with respect to the target tissue by measuring a first impedance value of the targeted tissue between the advanced flexible needle and an electrode on the delivery catheter;

delivering medical fluid through the flexible needle to the targeted tissue along the first pathway after verifying the position of the delivery catheter;

measuring a second impedance value of the targeted tissue; and verifying a position of the delivery catheter with respect to the targeted tissue by comparing the first impedance value and the second impedance value.

11. A method of delivering medical fluid to a tissue, the method comprising:

navigating a delivery catheter body through a vasculature to a fixation site proximate a targeted tissue;

fixing the delivery catheter body to the fixation site using a fixation member extending from a distal end of the delivery catheter body and having a central axis that extends through the central axis of the delivery catheter body;

advancing a first flexible needle out from a distal port located on the delivery catheter body, the first flexible needle extending away from the delivery catheter body central axis and along a first pathway within the targeted tissue;

advancing a second flexible needle out from a port located on the delivery catheter body, the second flexible needle extending away from the delivery catheter body central axis and along a second pathway within the targeted tissue;

measuring a first impedance value between the advanced first flexible needle and an electrode on the delivery catheter;

measuring a second impedance value between the advanced second flexible needle and a second electrode on the delivery catheter;

verifying the position of the delivery catheter with respect to the target tissue by comparing the first impedance value of the targeted tissue with the second impedance value of the targeted tissue; and delivering medical fluid through the first and/or second flexible needle to the targeted tissue after verifying the position of the delivery catheter, wherein verifying the position of the delivery catheter with respect to the targeted tissue further comprises determining that the delivery catheter is canted with respect to the surface of a targeted tissue.

12. A method of delivering medical fluid to a tissue, the method comprising:

navigating a delivery catheter body through a vasculature to a fixation site proximate a targeted tissue;

fixing the delivery catheter body to the fixation site using a fixation member extending from a distal end of the delivery catheter body and having a central axis that extends through the central axis of the delivery catheter body;

advancing a first flexible needle out from a distal port located on the delivery catheter body, the first flexible needle extending away from the delivery catheter body central axis and along a first pathway within the targeted tissue;

advancing a second flexible needle out from a port located on the delivery catheter body, the second flexible needle extending away from the delivery catheter body central axis and along a second pathway within the targeted tissue;

measuring a first impedance value between the advanced first flexible needle and an electrode on the delivery catheter;

measuring a second impedance value between the advanced second flexible needle and a second electrode on the delivery catheter;

verifying the position of the delivery catheter with respect to the target tissue by comparing the first impedance value of the targeted tissue with the second impedance value of the targeted tissue; and delivering medical fluid through the first and/or second flexible needle to the targeted tissue after verifying the position of the delivery catheter, wherein the electrode on the delivery catheter comprises the fixation member.

* * * * *